(12) United States Patent
Cadra et al.

(10) Patent No.: US 10,040,756 B2
(45) Date of Patent: Aug. 7, 2018

(54) SPECIFIC SULFONATE COMPOUNDS THAT CAN BE USED AS ELECTROLYTE SOLVENT FOR LITHIUM BATTERIES

(71) Applicant: RENAULT S.A.S., Boulogne-Billancourt (FR)

(72) Inventors: Stephane Cadra, Saint Avertin (FR); Charlotte Beord, Saint Avertin (FR); Nathalie Pierre, Monts (FR); Herve Galiano, La Ville aux Dames (FR)

(73) Assignee: RENAULT s.a.s., Boulogne-Billancourt (FR)

( * ) Notice: Subject to any disclaimer, the term of this patent is extended or adjusted under 35 U.S.C. 154(b) by 149 days.

(21) Appl. No.: 14/778,487

(22) PCT Filed: Feb. 18, 2014

(86) PCT No.: PCT/FR2014/050339
§ 371 (c)(1),
(2) Date: Sep. 18, 2015

(87) PCT Pub. No.: WO2014/154963
PCT Pub. Date: Oct. 2, 2014

(65) Prior Publication Data
US 2016/0137597 A1    May 19, 2016

(30) Foreign Application Priority Data
Mar. 20, 2013    (FR) ..................... 13 52493

(51) Int. Cl.
| | |
|---|---|
| H01M 10/05 | (2010.01) |
| C07C 309/65 | (2006.01) |
| H01M 10/0569 | (2010.01) |
| H01M 4/485 | (2010.01) |
| H01M 4/505 | (2010.01) |
| H01M 4/525 | (2010.01) |
| H01M 10/0525 | (2010.01) |
| C07C 303/28 | (2006.01) |
| H01M 10/052 | (2010.01) |
| H01M 10/0568 | (2010.01) |
| H01M 4/02 | (2006.01) |

(52) U.S. Cl.
CPC .......... *C07C 309/65* (2013.01); *C07C 303/28* (2013.01); *H01M 4/485* (2013.01); *H01M 4/505* (2013.01); *H01M 4/525* (2013.01); *H01M 10/052* (2013.01); *H01M 10/0525* (2013.01); *H01M 10/0568* (2013.01); *H01M 10/0569* (2013.01); *H01M 2004/027* (2013.01); *H01M 2004/028* (2013.01); *H01M 2300/0028* (2013.01); *Y02T 10/7011* (2013.01)

(58) Field of Classification Search
None
See application file for complete search history.

(56) References Cited

U.S. PATENT DOCUMENTS

| | | |
|---|---|---|
| 2004/0013946 A1 | 1/2004 | Abe et al. |
| 2004/0137333 A1 | 7/2004 | Nishiyama et al. |
| 2006/0286459 A1 | 12/2006 | Zhao et al. |
| 2010/0055576 A1 | 3/2010 | Abe |
| 2010/0062332 A1 | 3/2010 | Kumeuchi |
| 2010/0081052 A1* | 4/2010 | Morishima ........... H01M 2/263 429/211 |
| 2010/0221615 A1 | 9/2010 | Zhao et al. |
| 2011/0236737 A1 | 9/2011 | Zhao et al. |
| 2011/0306797 A1 | 12/2011 | Takeuchi et al. |
| 2012/0034532 A1 | 2/2012 | Kim et al. |
| 2013/0078509 A1 | 3/2013 | Zhao et al. |
| 2014/0168855 A1 | 6/2014 | Galiano et al. |
| 2014/0175326 A1 | 6/2014 | Galiano et al. |

FOREIGN PATENT DOCUMENTS

| | | | |
|---|---|---|---|
| CN | 102532228 A | * | 7/2012 |
| CN | 102532228 A | | 7/2012 |
| EP | 2 351 735 A1 | | 8/2011 |
| JP | 2007-73318 A | | 3/2007 |
| JP | 2007073318 A | * | 3/2007 |
| JP | 2007073318 A | * | 3/2007 |
| JP | 2012-190700 A | | 10/2012 |

OTHER PUBLICATIONS

JP 2007-073318 A machine English translation.*

(Continued)

*Primary Examiner* — Scott J Chmielecki
(74) *Attorney, Agent, or Firm* — Oblon, McClelland, Maier & Neustadt, L.L.P.

(57) ABSTRACT

The invention relates to sulfonate compounds with the following formula (I):

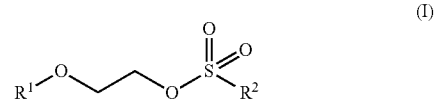

in which:

$R^2$ represents an ethyl group, an n-propyl group or an isopropyl group;

when $R^2$ is an ethyl group, $R^1$ is an ethyl group, an n-propyl group or an n-butyl group;

when $R^2$ is an n-propyl group, $R^1$ is a methyl group, an ethyl group, an n-propyl group or an n-butyl group; or when $R^2$ is an isopropyl group, $R^1$ is a methyl group, an ethyl group, an n-propyl group or an n-butyl group.

Use of these compounds as electrolyte solvent for lithium batteries.

13 Claims, No Drawings

(56) References Cited

OTHER PUBLICATIONS

Machine English translation of CN-102532228-A (Year: 2012).*
Machine English translation of JP 2007-073318 A (Year: 2007).*
Claudia C. Cassol, et al., "A Simple and Practical Method for the Preparation and Purity Determination of Halide-Free Imidazolium Ionic Liquids", Advanced Synthesis & Catalysis, vol. 348, No. 1-2, pp. 243-248, (Jan. 1, 2006), XP55012226.
Xiao-Guang Sun, et al., "New sulfone electrolytes for rechargeable lithium batteries. Part I. Oligoether-containing sulfones", Electrochemistry Communications, vol. 7, pp. 261-266, (2005).
Kang Xu, et al., "Sulfone-Based Electrolytes for Lithium-Ion Batteries", Journal of the Electrochemical Society, vol. 149, No. 7, pp. A920-A926, (Jan. 1, 2002), XP002607636.
V. B. Kazhdan, et al., "Synthesis and Repellent Properties of N-Alkylanilides and Esters of Butanesulfonic Acid", Pharmaceutical Chemistry Journal, vol. 6, No. 2, pp. 71-74, (Feb. 1, 1972), XP55084462.
F. L. M. Pattison, et al., "The Preparation and Some Cleavage Reactions of Alkyl and Substituted Alkyl Methanesulphonates", Canadian Journal of Chemistry, vol. 34, Total 12 Pages (Jan. 1, 1956), XP55084494.
International Search Report dated Jun. 20, 2014 in PCT/FR14/050339 Filed Feb. 18, 2014.
French Search Report dated Oct. 23, 2013 in French Application No. 1352493 Filed Mar. 20, 2013.
U.S. Appl. No. 14/127,344, filed Feb. 12, 2014, US-2014-0175326-A1, Herve Galiano et al.
U.S. Appl. No. 14/237,091, filed Feb. 4, 2014, US-2014-0168855-A1, Herve Galiano et al.

* cited by examiner

SPECIFIC SULFONATE COMPOUNDS THAT CAN BE USED AS ELECTROLYTE SOLVENT FOR LITHIUM BATTERIES

TECHNICAL FIELD

This invention relates to specific sulfonate compounds and their method of preparation and their use as solvents that are suitable particularly for dissolution of lithium salts.

Therefore it is quite natural that these compounds can be used in the field of electrolytes and particularly electrolytes intended for use in the composition of lithium batteries.

Lithium batteries are particularly useful for fields in which endurance is an overriding criterion, as is the case in the computer, video, mobile telephony and transport industries such as for electrical vehicles, hybrid vehicles and for medical, spatial and microelectronics fields.

Functionally, lithium batteries are based on the principle of intercalation-deintercalation of lithium within materials forming electrodes of the electrochemical cells of the battery.

More precisely, the reaction at the origin of current production (in other words when the battery is in discharge mode) involves the transfer of lithium cations from a negative electrode through an electrolyte conducting lithium ions, and these lithium cations then intercalate in the positive electrode acceptor network, while electrons derived from the reaction at the negative electrode will supply power to the external circuit to which the positive and negative electrodes are connected.

These electrolytes may consist of a mixture comprising at least one organic solvent and at least one lithium salt to achieve conduction of said lithium ions, which means that the lithium salt must be dissolved in said organic solvent.

This organic solvent may be a solvent forming part of the family of carbonates, carboxylates, linear or cyclic ethers, to which additives are added such as:
- sultone compounds in combination with vinylene carbonates as disclosed in US 2004/0137333, intended to protect non-graphitisable carbonated anodes from the formation of protuberances on their surface;
- mononitrile or dinitrile compounds in combination with compounds comprising a —S═O group as disclosed in US 2004/0013946 to reduce erosion phenomena of internal metallic elements included in a battery;
- cyclic sulfonate ester compounds comprising two sulfonyl groups or linear sulfonate ester compounds comprising two sulfonyl groups as disclosed in US 2010/0062332, designed to protect the negative electrode made of graphite from deposition phenomena of lithium compounds during the first charge;
- (di)-tert-butylphenyl-alkylsulfonate or (di)-tert-butylphenyl-arylsulfonate compounds as disclosed in US 2010/0055576, in order to improve cycling performances of a lithium battery;
- siloxane compounds in combination with sulfonate compounds comprising a 1,3-dioxane group as disclosed in US 2012/0034532, intended to limit phenomena causing long term degradation to the capacity of batteries used.

As is clear from the above, electrolytes may have a relatively complex nature in that they may require the presence of one or several additives in addition to the presence of one or several organic solvents and one or several lithium salts.

The inventors of this invention thus wished to develop new compounds with the following characteristics:
- compounds that can be used as solvents in the composition of electrolytes for lithium batteries;
- compounds that have properties adapted for the composition of an electrolyte in terms of viscosity (for example viscosity less than 10 mPa·s), with a dielectric constant (for example more than 20), conductivity (for example conductivity more than 1 mS/cm) while remaining stable for high operating potentials ($E_{ox}$>5V vs Li);
- compounds to limit or even eliminate the presence of electrolyte additives;
- compounds that, once associated with a lithium salt such as $LiPF_6$, can be used to obtain electrolytes with attractive properties (such as a conductivity of more than 1 mS/cm, a melting temperature lower than −20° C.).

Presentation of the Invention

Thus, the invention relates to sulfonate compounds with the following formula (I):

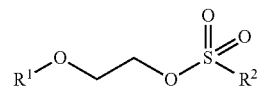

(I)

in which:
$R^2$ represents an ethyl group, an n-propyl group or an isopropyl group;
when $R^2$ is an ethyl group, $R^1$ is an ethyl group, an n-propyl group or an n-butyl group;
when $R^2$ is an n-propyl group, $R^1$ is a methyl group, an ethyl group, an n-propyl group or an n-butyl group; or
when $R^2$ is an isopropyl group, $R^1$ is a methyl group, an ethyl group, an n-propyl group or an n-butyl group.

The following compounds satisfy this specificity:
a compound for which $R^2$ is an n-propyl group and $R^1$ is a methyl group, this compound satisfies the following formula (II):

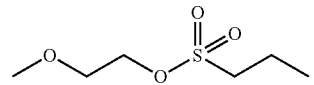

(II)

a compound for which $R^2$ is an n-propyl group and $R^1$ is an ethyl group, this compound satisfies the following formula (III):

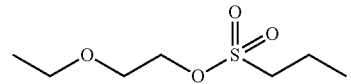

(III)

a compound for which $R^2$ is an ethyl group and $R^1$ is an ethyl group, this compound satisfies the following formula (IV):

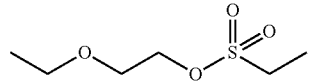

(IV)

Sulfonate compounds according to the invention can be prepared by the use of a method including a reaction step between a hydroxyether compound with formula $R^1$—O—$CH_2$—$CH_2$—OH, $R^1$ being as defined above with an X—$SO_2$—$R^2$ compound, where X is a halogen atom such as chlorine and $R^2$ is as defined above, in a medium comprising at least one base and one organic solvent, more specifically an aprotic organic solvent.

Said base may be:
- an amine compound such as trimethylamine, triethylamine, tri(n-butyl)amine;
- a pyridine compound such as pyridine; or
- an imidazole compound such as imidazole.

Said organic solvent may be an aliphatic hydrocarbon solvent, an aromatic solvent or a cyclic or acyclic ether solvent.

The reaction between the alcoholic compound with formula $R^1$—O—$CH_2$—$CH_2$—OH and the compound with formula X—$SO_2$—$R^2$ conventionally takes place at ambient temperature after these compounds have been brought into contact at a sub-ambient temperature.

At the end of this reaction step, the method for preparation of the compounds according to the invention may include a step to purify the compound obtained, this purification step possibly consisting of:
- a volatilisation step of the volatile compounds followed by a low pressure distillation step; or
- a purification step by chromatography on silica gel.

Among other properties, the compounds according to this invention have an oxidation potential of more than 5 V relative to the $Li^+/Li$ pair, low viscosity (less than 10 mPa·s), a high dielectric constant (more than 20) and a sub-ambient melting temperature. Furthermore, the compounds according to the invention have a good capability of solubilising lithium salts.

Therefore it is quite natural that they should be used in applications as an organic electrolyte solvent, and more particularly as an organic solvent that can be used in the composition of an electrolyte comprising at least one lithium salt intended for use in a lithium battery.

Thus, the invention also relates to:
- use of a compound as defined above as an organic solvent of at least one lithium salt, particularly as an organic solvent of at least one lithium salt in a lithium ion conducting electrolyte;
- a composition, more specifically a liquid composition, that may be a lithium ion conducting electrolyte comprising at least one compound as defined above and at least one lithium salt; and
- a lithium battery comprising at least one electrochemical cell comprising a lithium ion conducting electrolyte as defined above located between a positive electrode and a negative electrode.

For example, the lithium salt may be chosen from the group composed of $LiPF_6$, $LiClO_4$, $LiBF_4$, $LiAsF_6$, $LiCF_3SO_3$, $LiN(CF_3SO_2)_3$, $LiN(C_2F_5SO_2)$, lithium bistrifluoromethylsulfonylimide (known by the abbreviation LiTFSI) $LiN[SO_2CF_3]_2$ and mixes of them. More specifically, the lithium salt may be $LiPF_6$ or LiTFSI.

The above-mentioned composition may be composed exclusively of at least one compound according to the invention and at least one lithium salt or it may also comprise an aprotic cosolvent such as a carbonate solvent, a nitrile solvent or a sulfone solvent.

In the lithium battery, the above-mentioned liquid electrolyte in electrochemical cells of lithium batteries may be made to impregnate a separator located between the positive electrode and the negative electrode of the electrochemical cell.

This separator may be made of a porous material such as a polymeric material that can hold the liquid electrolyte in its pores. More specifically it may be a Celguard 2400 type membrane.

Conventionally, a positive electrode in the above and in the following description is the electrode that acts as the cathode when the generator outputs current (in other words during the discharge process), and that acts as the anode when the generator is in the charging process.

Conventionally, a negative electrode in the above and in the following description is the electrode that acts as the anode when the generator outputs current (in other words during the discharge process), and that acts as the cathode when the generator is in the charging process.

Advantageously, the negative electrode may be a material based on a lithium titanium oxide such as $Li_4Ti_5O_{12}$, that forms the lithium insertion material, said oxide may be dispersed in a polymeric binder, for example a vinylidene polyfluoride binder.

The positive electrode may be a material based on a lithium transition metal oxide (for example the metal could be nickel, manganese), and more specifically $LiMn_{2-z}Ni_zO_4$ (where 0<z<2), said oxide may be dispersed in a polymeric binder, for example a vinylidene polyfluoride binder.

The negative electrode and the positive electrode are advantageously each associated with a metallic current collector, for example an aluminium current collector.

The invention will now be described with reference to the following examples given as non-limitative examples for information.

DETAILED DESCRIPTION OF PARTICULAR EMBODIMENTS

EXAMPLE 1

This example illustrates the preparation of a compound conforming with the invention, 2-methoxyethyl propane-1-sulfonate, this preparation can be illustrated by the following reaction diagram:

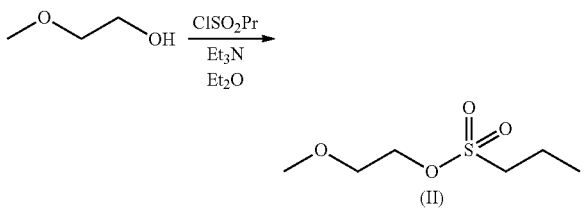

20 mL of anhydrous ether, 1.6 mL (20 mmol) of methoxyethanol and 4.2 mL (30 mmol) triethylamine are added into a 50 mL triple-neck round-bottomed flask purged with argon. The mixture is homogenised and cooled to 0° C. (ice bath). 2.25 mL (20 mmol) of propanesulfonyl chloride is introduced drop by drop using a syringe, which causes a slight increase in the mixture temperature due to the exothermic nature of the reaction. A few minutes after the addition, the ice bath is withdrawn and stirring is continued for 24 hours at ambient temperature.

At the end of the reaction, the mixture is filtered and the filtrate is extracted with a 1M hydrochloric acid solution. The organic phase is recovered, dried and evaporated (at 400 mbars). The residue is distilled at low pressure. The resulting product is a colourless liquid (Yield 67%).

The product was analysed by $^1$H NMR and $^{13}$C NMR and corresponds to the above-mentioned compound with formula (II).

The results are as follows:
$^1$H NMR (CDCl$_3$): 1.00 (t, 3H); 1.82 (sext, 2H); 3.05 (t, 2H); 3.32 (s, 3H); 3.57 (t, 2H); 4.26 (t, 2H).
$^{13}$C NMR (CDCl$_3$): 12.79; 17.13; 52.18; 58.94; 68.53; 70.40.

This compound has the following properties:
Melting point: below −90° C.
Boiling point: 280° C.
Viscosity: 6.78 mPa·s;
Dielectric constant: 32.

When an electrolyte is formed by dissolution of LiPF$_6$ (1.52 g, 10 mmol) in 10 mL of the above-mentioned sulfonate compound under an inert atmosphere in a glove box followed by stirring until complete dissolution of the salt, a melting point very much lower than −20° C. (more precisely, the melting point is of the order of −80° C.) is measured for the electrolyte obtained, giving excellent anti-freeze properties. A conductivity of 1.26 mS/cm and a viscosity of 34.2 mPa·s, are also obtained, both measured at 20° C. This confirms the ability of compositions according to the invention to have a high conductivity with high viscosity.

When an electrolyte is formed by dissolution of LiN(SO$_2$CF$_3$)$_2$ (symbolised by LiTFSI) (2.87 g, 10 mmol) in 10 mL of the above-mentioned sulfonate compound under an inert atmosphere in a glove box followed by stirring until complete dissolution of the salt, a melting point very much lower than −20° C. (more precisely, the melting point is of the order of −80° C.) is measured for the electrolyte obtained, giving excellent anti-freeze properties. A conductivity of 1.17 mS/cm and a viscosity of 23.5 mPa·s, are also obtained, both measured at 20° C.

EXAMPLE 2

This example illustrates the preparation of a compound conforming with the invention: 2-ethoxyethyl propane-1-sulfonate, this preparation being illustrated by the following reaction diagram:

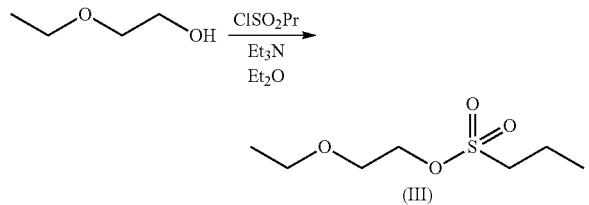

20 mL of anhydrous ether, 2.0 mL (20 mmol) of ethoxyethanol and 4.2 mL (30 mmol) triethylamine are added into a 50 mL triple-neck round-bottomed flask purged with argon. The mixture is homogenised and cooled to 0° C. (ice bath). 2.25 mL (20 mmol) of propanesulfonyl chloride is introduced drop by drop using a syringe, which causes a slight increase in the mixture temperature due to the exothermic nature of the reaction. A few minutes after the addition, the ice bath is withdrawn and stirring is continued for 24 hours at ambient temperature.

At the end of the reaction, the mixture is filtered and the filtrate is extracted with a solution of 1M hydrochloric acid. The organic phase is recovered, dried and evaporated (at 400 mbars). The residue is distilled at low pressure. The resulting product is a translucid liquid (Yield 81%).

The product was analysed by $^1$H NMR and $^{13}$C NMR.
The results are as follows:
$^1$H NMR (CDCl$_3$): 1.05 (t, 3H); 1.18 (t, 3H); 1.89 (next, 2H); 3.11 (t, 2H); 3.52 (quad, 2H); 3.66 (t, 2H); 4.32 (t, 2H).
$^{13}$C NMR (CDCl$_3$): 12.69; 14.89; 17.08; 52.02; 66.61; 68.21; 68.86.

This compound has the following properties:
Melting point: below −90° C.;
Boiling point: 290° C.;
Viscosity (mPa·s): 6.52;
Dielectric constant: 32.

EXAMPLE 3

This example illustrates the preparation of a compound conforming with the invention: 2-ethoxyethyl ethane-1-sulfonate, this preparation being illustrated by the following reaction diagram:

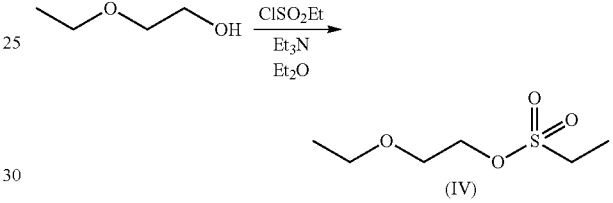

20 mL of anhydrous ether, 2.0 mL (20 mmol) of ethoxyethanol and 4.2 mL (30 mmol) triethylamine are added into a 50 mL triple-neck round-bottomed flask purged with argon. The mixture is homogenised and cooled to 0° C. (ice bath). 2.25 mL (20 mmol) of ethanesulfonyl chloride is introduced drop by drop using a syringe, which causes a slight increase in the mixture temperature due to the exothermic nature of the reaction. A few minutes after the addition, the ice bath is withdrawn and stirring is continued for 24 hours at ambient temperature.

At the end of the reaction, the mixture is filtered and the filtrate is extracted with a solution of 1M hydrochloric acid. The organic phase is recovered, dried and evaporated (at 400 mbars). The residue is distilled at low pressure. The resulting product is a translucid liquid (Yield 64%).

The product was analysed by $^1$H NMR and $^{13}$C NMR and corresponds to the above-mentioned compound with formula (IV).

The results are as follows:
$^1$H NMR (CDCl$_3$): 1.09 (t, 3H); 1.30 (t, 3H); 3.08 (quad, 2H); 3.44 (quad, 2H); 3.58 (t, 2H); 4.23 (t, 2H).
$^{13}$C NMR (CDCl$_3$): 9.28; 13.02; 17.50; 26.89; 53.25; 85.48.

This compound has the following properties:
Melting point: below −90° C.;
Boiling point: 280° C.;
Viscosity (mPa·s): 7.3;
Dielectric constant: 40.

When an electrolyte is formed by dissolution of LiPF$_6$ (1.52 g, 10 mmol) in 10 mL of the above-mentioned sulfonate compound under an inert atmosphere in a glove box followed by stirring until complete dissolution of the salt, a melting point very much lower than −20° C. (more precisely, the melting point is below −80° C.) is measured for the electrolyte obtained, giving excellent anti-freeze properties. A conductivity of 1.23 mS/cm and a viscosity of 34 mPa·s, are also obtained, both measured at 20° C.

When an electrolyte is formed by dissolution of LiN(SO$_2$CF$_3$)$_2$ (symbolised by LiTFSI) (2.87 g, 10 mmol) in 10 mL of the above-mentioned sulfonate compound under an inert atmosphere in a glove box followed by stirring until complete dissolution of the salt, a melting point very much lower than −20° C. (more precisely, the melting point is below −80° C.) is measured for the electrolyte obtained, giving excellent anti-freeze properties. A conductivity of 1.14 mS/cm and a viscosity of 23.5 mPa·s, are also obtained, both measured at 20° C.

The invention claimed is:

1. A composition composed exclusively of a sulfonate compound and at least one lithium salt, said sulfonate compound being of formula (I):

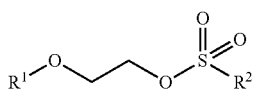

(I)

wherein
R$^2$ is an ethyl group, an n-propyl group or an isopropyl group,
wherein:
when R$^2$ is an ethyl group, R$^1$ is an ethyl group, an n-propyl group or an n-butyl group;
when R$^2$ is an n-propyl group, R$^1$ is a methyl group, an ethyl group, an n-propyl group or an n-butyl group; and
when R$^2$ is an isopropyl group, R$^1$ is a methyl group, an ethyl group, an n-propyl group or an n-butyl group,
wherein the sulfonate compound is an organic solvent of the at least one lithium salt.

2. The composition according to claim 1, wherein R$^2$ is an n-propyl group and R$^1$ is a methyl group.

3. The composition according to claim 1, wherein R$^2$ is an n-propyl group and R$^1$ is an ethyl group.

4. The composition according to claim 1, wherein R$^2$ is an ethyl group and R$^1$ is an ethyl group.

5. The composition according to claim 1, wherein the lithium salt is at least one selected from the group consisting of LiPF$_6$, LiClO$_4$, LiBF$_4$, LiAsF$_6$, LiCF$_3$SO$_3$, LiN(CF$_3$SO$_2$)$_3$, LiN(C$_2$F$_5$SO$_2$), lithium bistrifluoromethylsulfonylimide LiN[SO$_2$CF$_3$]$_2$ and mixtures thereof.

6. A lithium battery comprising an electrochemical cell comprising the composition according to claim 1, which is an electrolyte, located between a positive electrode and a negative electrode.

7. The lithium battery according to claim 6, wherein the negative electrode is a material comprising a lithium titanium oxide.

8. The lithium battery according to claim 6, wherein the positive electrode is a material comprising a material of formula LiMn$_{2-z}$Ni$_z$O$_4$, where 0<z<2.

9. A sulfonate compound of fonnula (I):

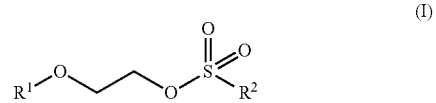

(I)

wherein:
R$^2$ is an ethyl group, an n-propyl group or an isopropyl group,
wherein:
when R$^2$ is an ethyl group, R$^1$ is an n-propyl group or an n-butyl group;
when R$^2$ is an n-propyl group, R$^1$ is an ethyl group, an n-propyl group or an n-butyl group; and
when R$^2$ is an isopropyl group, R$^1$ is an ethyl group, an n-propyl group or an n-butyl group.

10. The sulfonate compound according to claim 9, wherein R$^2$ is an n-propyl group and R$^1$ is an ethyl group.

11. The composition according claim 1, wherein R$^2$ is an n-propyl group and R$^1$ is a methyl group.

12. The composition according to claim 1, wherein R$^2$ is an n-propyl group and R$^1$ is an ethyl group.

13. The composition according to claim 1, wherein R$^2$ is an ethyl group and R$^1$ is an ethyl group.

* * * * *